United States Patent
Epstein et al.

(10) Patent No.: US 8,911,963 B2
(45) Date of Patent: Dec. 16, 2014

(54) CONDITIONED MEDIUM OBTAINED FROM STEM CELLS AND ITS USE IN THERAPY

(75) Inventors: Stephen E. Epstein, Rockville, MD (US); Mary Susan Burnett, Burke, VA (US); Amir Najafi, Potomac, MD (US)

(73) Assignee: MedStar Health Research Institute, Inc., Washington, DC (US)

( * ) Notice: Subject to any disclaimer, the term of this patent is extended or adjusted under 35 U.S.C. 154(b) by 0 days.

(21) Appl. No.: 13/639,380

(22) PCT Filed: Apr. 5, 2011

(86) PCT No.: PCT/US2011/031299
§ 371 (c)(1),
(2), (4) Date: Jan. 17, 2013

(87) PCT Pub. No.: WO2011/127090
PCT Pub. Date: Oct. 13, 2011

(65) Prior Publication Data
US 2013/0110132 A1    May 2, 2013

(51) Int. Cl.
| | | |
|---|---|---|
| C12P 1/00 | (2006.01) | |
| C12N 5/00 | (2006.01) | |
| A61K 38/18 | (2006.01) | |
| A61K 35/28 | (2006.01) | |
| A61L 27/38 | (2006.01) | |
| A61B 17/50 | (2006.01) | |
| A61L 27/60 | (2006.01) | |
| A61K 35/12 | (2006.01) | |

(52) U.S. Cl.
CPC ............ *A61K 38/1891* (2013.01); *A61K 35/28* (2013.01); *A61L 27/3895* (2013.01); *A61B 17/50* (2013.01); *A61L 27/3834* (2013.01); *A61L 27/60* (2013.01); *A61K 35/35* (2013.01)
USPC ........................................... 435/41; 435/325

(58) Field of Classification Search
USPC .................................................. 435/41, 325
See application file for complete search history.

(56) References Cited

U.S. PATENT DOCUMENTS

| | | | |
|---|---|---|---|
| 6,372,494 B1 * | 4/2002 | Naughton et al. | 435/391 |
| 2006/0211600 A1 * | 9/2006 | Dzau et al. | 514/2 |

FOREIGN PATENT DOCUMENTS

| | | |
|---|---|---|
| WO | WO 2006/029262 | 3/2006 |
| WO | WO 2006/060779 | 6/2006 |
| WO | WO 2008/020815 | 2/2008 |

OTHER PUBLICATIONS

Guo et al. (Hypoxia-mimetic agents desferroxamine and cobalt chloride induce leukemic cell apoptosis through different hypoxia-inducible factor-1 alpha independent mechanisms. Apoptosis (2006) 11(1):67-77).*
Hung et al. "Angiogenic effects of human multipotent stromal cell conditioned medium activate the PI3K-Akt pathway in hypoxic endothelial cells to inhibit apoptosis, increase survival, and stimulate angiogenesis" Stem Cells. Sep. 2007;25(9):2363-70.
Kinnaird et al. "Marrow-derived stromal cells express genes encoding a broad spectrum of arteriogenic cytokines and promote in vitro and in vivo arteriogenesis through paracrine mechanisms" Circ Res. Mar. 19, 2004;94(5):678-85.
Shen et al. "Prolyl hydroxylase inhibitors increase neoangiogenesis and callus formation following femur fracture in mice" J Orthop Res. Oct. 2009;27(10):1298-305.
Sun et al. "Sustained release of multiple growth factors from injectable polymeric system as a novel therapeutic approach towards angiogenesis" Pharm Res. Feb. 2010;27(2):264-71.
Yoon et al. "Secretory profiles and wound healing effects of human amniotic fluid-derived mesenchymal stem cells" Stem Cells Dev. Jun. 2010;19(6):887-902.

* cited by examiner

Primary Examiner — Karen Cochrane Carlson
Assistant Examiner — Natalie Moss
(74) Attorney, Agent, or Firm — Wolf, Greenfield & Sacks, P.C.

(57) ABSTRACT

Described herein are conditioned medium and processed conditioned medium, each of which comprises secreted stem cell factors; compositions containing conditioned medium and/or processed conditioned medium and a delivery polymer. The conditioned medium, processed conditioned medium and compositions may be used to promote blood vessel growth and healing of injured tissues.

10 Claims, 16 Drawing Sheets

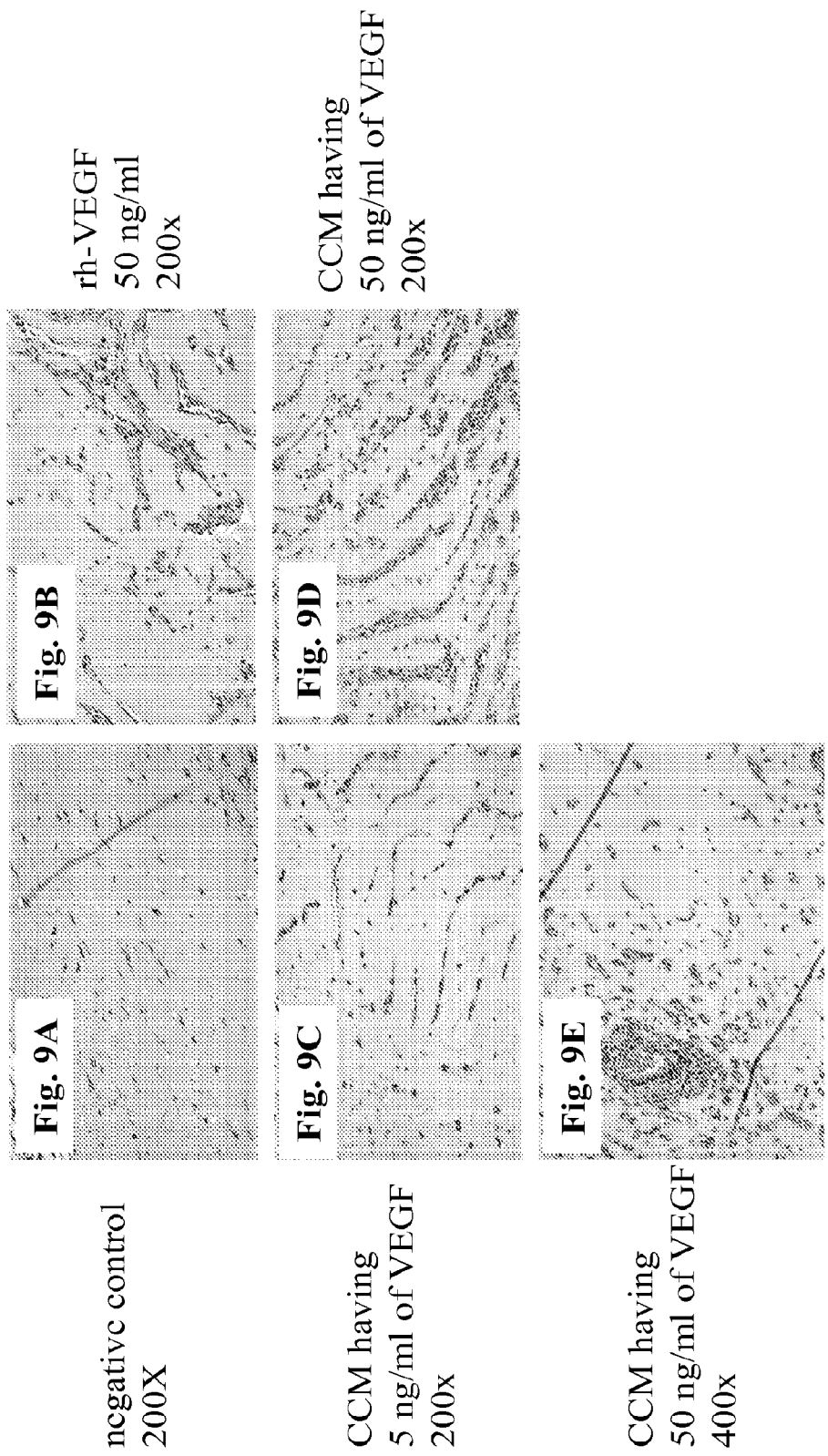

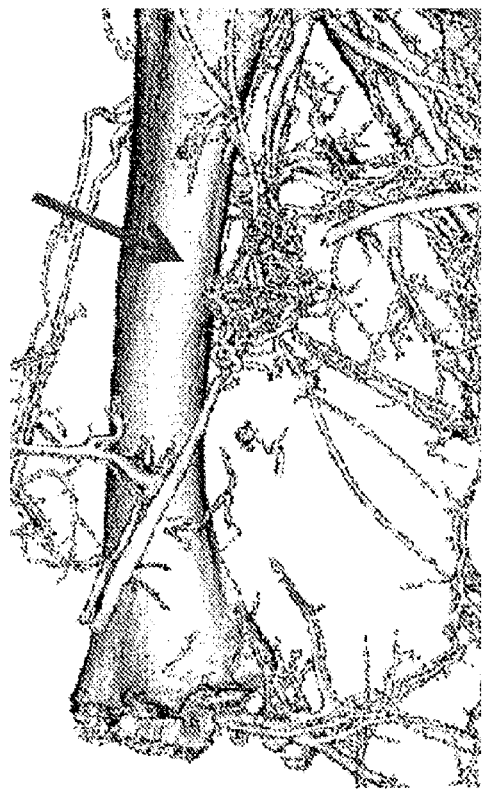
Fig. 11

Advancement of Catheter Through Chronic Total Occlusion
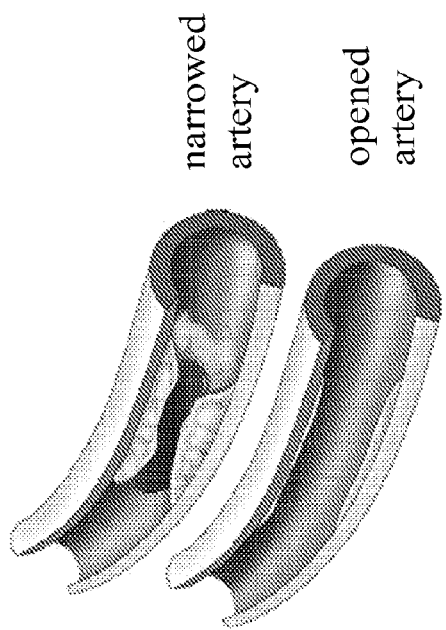
narrowed artery
opened artery
Fig. 12A
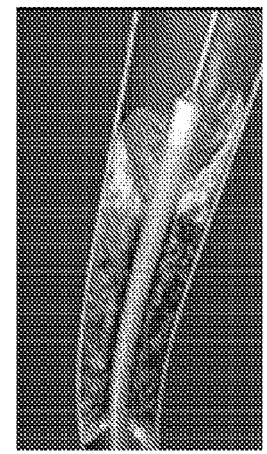
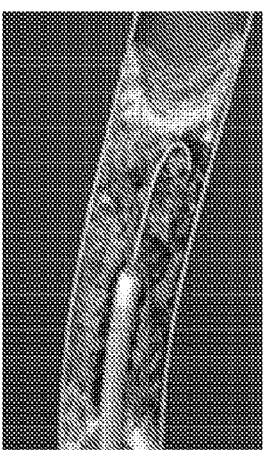
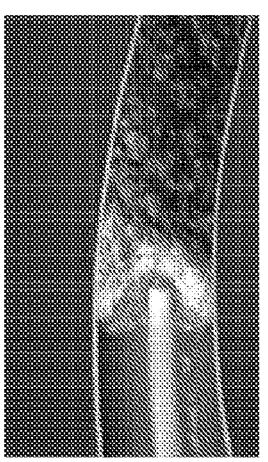
Fig. 12B

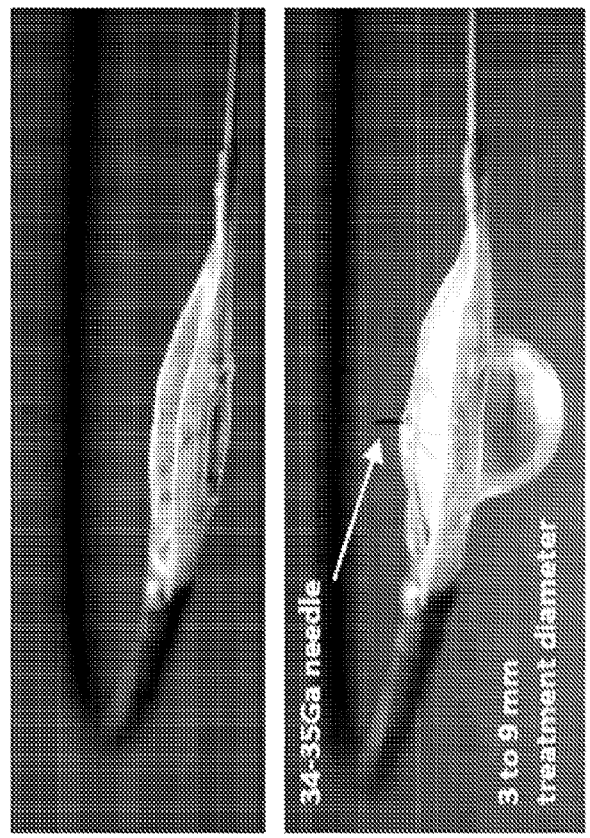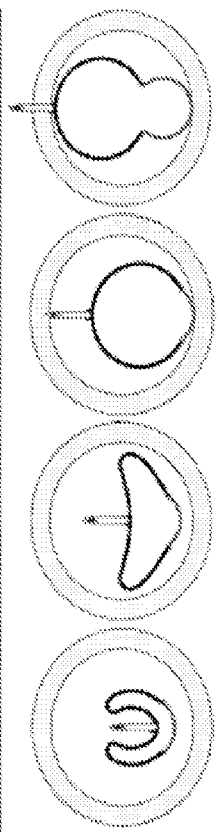
Fig. 13

Facilitate Healing in Injured Tissue – Burn

CONDITIONED MEDIUM OBTAINED FROM STEM CELLS AND ITS USE IN THERAPY

RELATED APPLICATIONS

This application is a national phase filing under 35 U.S.C. §371 of International Application No. PCT/US2011/031299, filed Apr. 5, 2011, which claims the benefit under 35 U.S.C. §119(e) of U.S. Provisional Application No. 61/320,937, filed Apr. 5, 2010, and of U.S. Provisional Application No. 61/356,135, filed Jun. 18, 2010. The entire teachings of each of the referenced provisional applications are incorporated herein by reference.

BACKGROUND

One of the major unmet needs in medicine today is a treatment for successfully augmenting collateral function in patients who have severe obstructions in arteries supplying their hearts or their legs. Another unmet need is a treatment for facilitating healing of injured tissue, including burned skin, broken bone, torn tendons, and decubitis ulcers. Each of these processes—the development of collaterals to bypass arterial obstructions and stimulation of new blood vessel development (angiogenesis) to facilitate wound healing—involves complex, multi-molecular processes that cannot simply be replicated by administration of, for example, a single growth factor.

Clearly, additional therapies are needed.

SUMMARY OF THE INVENTION

Described herein are compositions, including conditioned medium (CM) and processed conditioned medium (pCM); methods of producing conditioned medium and processed conditioned medium; and methods in which conditioned medium, processed conditioned medium or both conditioned medium and processed conditioned medium are administered in order, for example, to promote collateral development (angiogenesis) in a subject, treat chronic total occlusion of a blood vessel in a subject, treat injured tissue in a subject or treat a skin burn in a subject. The present invention enables introduction of stem cell factors to a selected site, such as a site of injury, without the need to administer stem cells and, thus, makes it possible to avoid the problems associated with their use.

In one aspect, provided herein are methods of producing processed conditioned medium, comprising (a) culturing stem cells in growth-factor-free medium comprising desferroxamine, thereby generating conditioned medium that comprises factors secreted by the stem cells; (b) harvesting conditioned medium thereby producing harvested conditioned medium; and (c) filtering harvested conditioned medium to produce processed conditioned medium. In certain embodiments, the stem cells of (a) are cultured (have been cultured) in growth medium prior to being cultured in growth factor-free medium. Thus, in some embodiments, the methods comprise: (a) culturing stem cells in growth medium; (b) replacing the growth medium with growth factor-free medium comprising desferroxamine and culturing the stem cells in the growth factor-free medium, thereby generating conditioned medium that comprises factors secreted by the stem cells; (c) harvesting conditioned medium, thereby producing harvested conditioned medium; and (d) filtering harvested conditioned medium to produce processed conditioned medium. In other embodiments, the methods include (a) obtaining stem cells previously cultured in growth medium; (b) culturing the stem cells in growth-factor-free medium comprising desferroxamine, thereby generating conditioned medium that comprises factors secreted by the stem cells; (c) harvesting conditioned medium, thereby producing harvested conditioned medium; and (d) filtering harvested conditioned medium to produce processed conditioned medium.

In particular embodiments, the filtering is by ultra-filtration. In some embodiments, the conditioned medium is filtered using a filter size of 3 kD (to achieve purification, desalting, and concentration in the processed conditioned medium of molecules larger than the filter size). In some embodiments, a filter size of less than 3 kD is used to filter the conditioned medium, while in other embodiments a filter size of greater than 3 kD is used, depending on the application for which the processed conditioned medium is used. In other embodiments, ultra-filtration of harvested conditioned medium is carried out using a filter of a different pore size (e.g., 2 kD, <2 kD or >2 kD) selected to determine the size of components of the resulting process conditioned medium.

In some embodiments, the processed conditioned medium comprises an increased concentration of angiogenic factors (relative to the concentration of angiogenic factors in conditioned medium from which the processed conditioned medium is produced). In certain embodiments, processed conditioned medium comprising an increased concentration of angiogenic factors can be used to promote collateral development in a subject, to treat chronic total occlusion in a subject, to treat injured tissue in a subject, or to treat skin burns in a subject.

In certain embodiments, the stem cells are isolated from bone marrow. In some embodiments, the bone marrow stem cells are mesenchymal (non-blood) stem cells, while in other embodiments, the bone marrow stem cells are hematopoietic (blood) stem cells. In other embodiments, the stem cells can be isolated from other tissues, such as adipose tissue.

In another aspect, provided herein is processed conditioned medium generated by any one of the foregoing methods and embodiments.

In yet another aspect, provided herein are compositions, including (a) processed conditioned medium produced by any one of the foregoing methods and embodiments; and (b) a polymer. Alternatively, a composition can comprise conditioned medium produced as described herein and a polymer or both conditioned medium and processed conditioned medium and a polymer. The polymer is typically a biodegradable polymer from which the conditioned medium and/or processed conditioned medium are released. In certain embodiments, the polymer enables sustained (slow) release of the processed conditioned medium In some embodiments, the compositions provided herein are in the form of a therapeutic bandage (e.g., a polymer impregnated with conditioned medium and/or processed conditioned medium). The therapeutic bandage may be configured as needed, depending on the application. In some embodiments, the bandage is in the form or a patch or is configured as mesh.

In some aspects, provided herein are methods of enhancing secretion of angiogenic factors by stem cells, including culturing the stem cells in growth factor-free medium comprising desferroxamine. In some embodiments, the stem cells are first (previously) cultured in growth medium. In some embodiments, the stem cells are isolated from bone marrow. In certain embodiments the bone marrow stem cells are mesenchymal stem cells, while in other embodiments they are hematopoietic stem cells. In other embodiments, the stem cells can be isolated from other tissues, such as adipose tissue.

In other aspects, provided herein are methods of promoting collateral development or angiogenesis in a subject (e.g., a human or a non-human, such as a farm animal or a domesticated animal), comprising administering to the subject conditioned medium and/or processed conditioned medium produced by any one of the foregoing methods and embodiments in an amount effective to promote collateral development. In still other aspects, provided are methods of promoting collateral development in a subject, comprising administering to the subject any of the compositions disclosed herein in an amount effective to promote collateral development. In some embodiments, the composition is administered by injection.

In certain aspects, provided herein are methods of treating chronic total occlusion of a blood vessel in a subject, comprising administering to the subject any of the compositions disclosed herein in an amount effective to treat occlusion, such as chronic total occlusion, of a blood vessel in the subject. In some embodiments, the composition is administered directly to the site of the chronic total occlusion. In some embodiments, the composition is administered by injection (e.g., needle and syringe). In certain embodiments, the methods include advancing a catheter into the occluded blood vessel of the subject. The catheter may be used for delivering an injection of the processed conditioned medium.

In other aspects, provided herein are methods of treating (e.g., healing or improving the condition of) injured tissue in a subject, comprising administering to the site of the injured tissue any of the compositions described herein in an amount effective to treat the injured tissue. In some embodiments, the composition is administered to the injured tissue by injection. In some embodiments, the injured tissue is burned skin, ruptured tendon, broken bone, or decubitis ulcer. In a particular embodiment, the injured tissue is burned skin.

In still other aspects, provided herein are methods of treating a skin burn in a subject, comprising administering to the subject any one of the described compositions. In some embodiments, the methods include removing dead skin from the site of the injured tissue, and applying a skin graft to underlying healthy tissue.

In some aspects, provided herein is processed conditioned medium produced by any of the methods described and embodiments for the promotion of collateral development in a subject, the treatment of chronic total occlusion in a subject, the treatment of injured tissue in a subject, or the treatment of skin burns in a subject. In certain embodiments, any one of the compositions described herein may be used for the promotion of collateral development in a subject, the treatment of chronic total occlusion in a subject, the treatment of injured tissue in a subject, or the treatment of skin burns in a subject.

BRIEF DESCRIPTION OF THE FIGURES

The figures are illustrative only and are not required for enablement of the invention disclosed herein.

FIG. 9 shows histological sections from mouse abdomen 14 days post subcutaneous implantation of concentrated (processed) CM-impregnated polymer. The data demonstrates that the CM-impregnated polymer is more efficient at stimulating blood vessel growth, as compared to VEGF alone.

FIG. 11 is a schematic of the general strategy for treating chronic total occlusion.

FIGS. 12A and 12B depict, respectively, a narrowed artery resulting from chronic total occlusion, and an open artery and advancement of a catheter through an obstructed/occluded artery.

FIG. 13 depicts a micro-infusion catheter that can be used to deliver the inventive CM-impregnated polymer to the site of artery occlusion/obstruction.

DETAILED DESCRIPTION OF THE INVENTION

Figure 1:
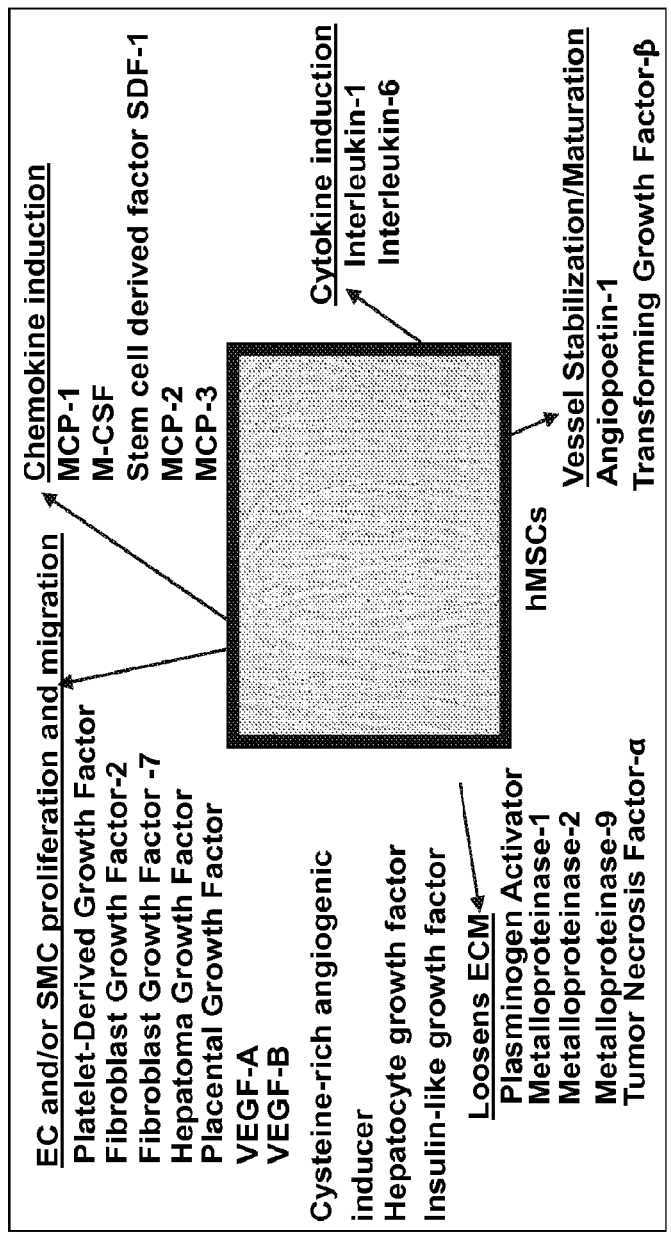
FIG. 1 depicts that human mesenchymal stem cells (hMSCs) derived from bone marrow secrete cytokines, which function in multiple biological pathways.

In one aspect, the present invention is directed to conditioned medium (CM) comprising biological factors secreted by stem cells. The conditioned medium is obtained by culturing stem cells in media, as described herein, and separating the resulting media, which contains stem cells and their secreted stem cell products (referred to as biological factors) into conditioned medium that contains biological factors and fewer stem cells than were present prior to separation. The conditioned medium may be used in the methods described herein and is substantially free of stem cells (may contain a small percentage of stem cells) or free of stem cells. Biological factors that may be in the conditioned medium include hormones, cytokines, extracellular matrix, proteins, vesicles, antibodies, chemokines, receptors, inhibitor, and granules. In certain embodiments, the conditioned medium (media) is processed, producing concentrated, processed conditioned medium (pCM). In some embodiments, the CM or pCM is produced by culturing stem cells in culture medium, replacing culture medium in which stem cells have been cultured in growth factor-free medium containing desferroxamine (DFO), and further culturing the stem cells in the growth factor-free/DFO medium. Alternatively, stem cells that have been previously cultured (e.g. cultured stem cells that have been stored or provided by a source such as another individual or a commercial source) can be further cultured in growth factor-free medium containing desferroxamine (DFO). In either case, the resultant medium is referred to as conditioned medium (CM). The resultant CM is harvested (collected), then processed to produce pCM. In certain embodiments, processing of the harvested CM includes removal of some, most, or essentially all of the medium, or removal of some, most, or essentially all of selected components of the conditioned medium.

In some embodiments, the harvested CM is filtered to produce pCM. In some embodiments, the harvested CM is ultra-filtered to produce pCM. CM or pCM may be used to treat a subject in need, such as a subject who has or is suspected of having arterial occlusive disease, a chronic total occlusion, or other injured tissue in need of healing or is at risk of myocardial infarction.

An injured tissue (wound or break) is a tissue having any disruption, from any cause, of normal anatomy (internal or external anatomy) including, but not limited to: traumatic injuries such as mechanical, thermal, and incisional injuries; elective injuries such as surgery and resultant incisional hernias; acute wounds, chronic wounds, infected wounds, and sterile wounds, as well as wounds associated with diseased states (e.g., ulcers or decubitus ulcers in subjects having impaired mobility). An injury to a tissue may be dynamic and the process of healing is a continuum requiring a series of integrated and interrelated cellular processes that begin at the time of injury and, in the instance of wounds, proceed beyond initial wound closure through arrival at a stable scar. These cellular processes are mediated or modulated by humoral substances including but not limited to cytokines, lymphokines, growth factors, and hormones. In accordance with the subject invention, tissue "healing" refers to improving, by administering conditioned medium, processed conditioned medium or both (which comprise stem cell growth factors), the natural cellular processes and humoral substances of tissue repair such that healing is faster, and/or the resulting healed area has less scaring and/or the wounded area possesses tissue strength that is closer to that of uninjured tissue and/or the wounded tissue attains some degree of functional recovery.

In certain embodiments, conditioned medium and processed conditioned medium (and, thus, stem cell secreted factors) can be obtained from stem cells obtained from the individual to be treated (the individual in need) or from another (donor) individual, such as a young and/or healthy donor. For example, bone marrow-derived stem cells obtained from the individual to be treated (autologous stem cells) or from a donor (allogeneic stem cells), can be used to produce the conditioned medium described herein.

In another aspect, the present invention is directed to increasing the amount of biological factors secreted by the stem cells, including culturing the stem cells in growth factor-free medium comprising desferroxamine (DFO) or other component which produces substantially the same effect as DFO. Desferroxamine, also known in the art as deferoxamine, desferrioxamine B, desferoxamine B, DFO-B, DFOA and desferal, stimulates the HIF signaling pathway and is also a chelator of iron (which inhibits the HIF-1 pathway). The increased amount of biological factors is relative to the amount of biological factors secreted by stem cells when grown in growth factor-free medium in the absence of DFO.

The term "stem cell" refers to an unspecialized cell capable of renewing itself through cell division and which, under certain physiologic or experimental conditions, can be induced to become a tissue- or organ-specific cell with special functions [website: stemcells.nih.gov]. However, cells that are somewhat differentiated (progenitor cells) can also be used. In certain embodiments, the stem cells herein are autologous or can be allogeneic stem cells.

In some embodiments, the stem cells are mesenchymal stem cells. Mesenchymal stem cells (MSCs) are multipotent (capable of differentiating into multiple, but not all, cell lineages) nonhematopoietic (non-blood) stem cells isolated from (derived from) a variety of adult tissues, including bone marrow and adipose tissue. "Isolated" refers to cells removed from their original environment. MSCs may differentiate into cells of mesodermal lineage, for example, adipocytes, osteoblasts, and chondrocytes. MSCs have a small cell body with few cell processes that are long and thin. The cell body contains a large, round nucleus with a prominent nucleolus, which is surrounded by finely dispersed chromatin particles, giving the nucleus a clear appearance. The remainder of the cell body contains a small amount of Golgi apparatus, rough endoplasmic reticulum, mitochondria, and polyribosomes. The cells, which are long and thin, are widely dispersed and the adjacent extracellular matrix is populated by a few reticular fibrils but is devoid of the other types of collagen fibrils [Brighton, et al. 1991 The Journal of Bone and Joint Surgery 73(6):832-47]. MSCs described herein may express the following molecular marker (protein molecule characteristic of plasma membrane of a cell or cell type) profiles: bone morphogenic protein receptor$^+$ (BMPR$^+$); CD34$^+$Sca1$^+$Lin$^-$; CD44$^+$; c-kit$^+$; Sca-1$^+$; Thy-1$^+$; NOTCH3; JAG1; ITGA11. MSCs may also express other cell type-specific markers [website: stemcells.nih.gov/info/scireport/appendixe.asp; Kaltz, et al. 2010 Exp Cell Res Oct 1; 316(16):2609-17, incorporated herein by reference]. MSCs described herein may be identified based on colony-forming unit assays to detect the multipotent differentiation potential of the MSCs (to what cell types the MSCs give rise). However, cells that are somewhat differentiated (progenitor cells) can also be used.

In some embodiments, the conditioned medium and processed conditioned medium are produced using a mixed population of MSCs and HSCs isolated from bone marrow. In other embodiments, the population of stem cells isolated from bone marrow may contain MSCs, HSCs, and additional cell populations present in bone marrow.

In certain embodiments the mesenchymal stem cells are isolated from bone marrow or from adipose tissue, while in other embodiments they are derived from induced pluripotent stem cells (e.g., somatic cells reprogrammed to enter an embryonic stem cell-like state by being forced to express factors important for maintaining the stem cell-like state) [Takahashi, et al. Cell 2007 Nov. 30; 131(5):861-72; Yu, et al. Science 2007 Dec. 21; 318(5858):1917-20, incorporated herein by reference].

In certain embodiments, the stem cells are hematopoietic stem cells. Hematopoietic stem cells (HSCs) are multipotent stem cells that give rise to the myeloid (monocytes and macrophages, neutrophils, basophils, eosinophils, erythrocytes, megakaryocytes/platelets, dendritic cells), and lymphoid lineages (T-cells, B-cells, NK-cells). HSCs are isolated from adult bone marrow, which includes femurs, hip, ribs, sternum, and other bones. They can be obtained directly by removal from the hip using a needle and syringe, or from the blood following pre-treatment with cytokines, such as G-CSF (granulocyte colony-stimulating factors), that induce cells to be released from the bone marrow compartment. Other sources for clinical and scientific use include umbilical cord blood, placenta, mobilized peripheral blood. HSCs may express the following molecular marker profiles: $CD34^+$; $c$-$kit^+$; $Lin^+$; and/or $Sca$-$1^+$[website: stemcells.nih.gov/info/scireport/appendixe.asp]. With regard to morphology, hematopoietic stem cells resemble lymphocytes. They are non-adherent, and rounded, with a rounded nucleus and low cytoplasm-to-nucleus ratio.

Stem cells produce factors, such as growth factors, that regulate or are important for regulating multiple biological processes. A growth factor is an agent, such as a naturally occurring substance capable of stimulating cellular growth and/or proliferation and/or cellular differentiation. Typically, growth factors are proteins or steroid hormones. "Growth factor" and "factor" may be used interchangeably; however, as used herein, the term "biological factor" is not limited to a growth factor. MSCs isolated from bone marrow produce factors involved in, for example, cell proliferation and migration (e.g., platelet-derived growth factor (PDGF), fibroblast growth factor (FGF)-1, FGF-7, hepatoma growth factor, placental growth factor (PlGF), vascular endothelial growth factor (VEGF)-A, VEGF-B), chemokine induction (e.g., MCP-1, MCP-2, MCP-3, M-CSF, stem cell derived factor-1 (SDF-1)), cytokine induction (e.g., interleukin (IL)-1, IL-6), blood vessel stabilization/maturation (e.g., angiopoetin-1 (ANG-1), transforming growth factor-β (TGF-β)), loosening of extracellular matrix (e.g., plasminogen activator, metalloproteinase-1, metalloproteinase-2, metalloproteinase-, tumor necrosis factor-α (TNF-α)), as well as other factors including cysteine-rich angiogenic inducer, hepatocyte growth factor, and insulin-like growth factor. All stem cells produce biological factors. Therefore, it follows that a wide variety of stem cells may be used to generate the conditioned medium (CM) and processed conditioned medium (pCM) of the present invention. CM and pCM of this invention comprise at least one and, more typically, a combination of biological factors produced by stem cells (e.g., at least one and. more typically, a combination of biological factors listed above). For example, they can comprise one or more (at least one) angiogenic cytokines and/or growth factors. They can comprise one or more of PGF, FGF7, Hepatoma Growth Factor, PlGF, cysteine-rich angiogenic inducer, Hepatocyte Growth Factor, Insulin-like Growth Factor, M-CSF, SDF-1, MCP-2, MCP-3, IL-1, IL-6, TGF-B, Angiopoetin-1 VEGF, MCP-1, Ang-1, Ang-2, FGF2 and PDGF-β.

In some embodiments, the stem cells are grown to high confluence (density) in an appropriate culture medium before the growth medium is replaced with growth factor-free medium. In other embodiments the stem cells are grown as a single confluent layer. In some embodiments, the growth factor-free medium is serum-free and phenol red-free DMEM (Dulbecco's Modified Eagle Medium). In specific embodiments, the growth factor-free medium is serum-free and phenol red-free DMEM and further includes desferroxamine (DFO). In some embodiments the concentration of DFO is greater than 1 micromolar, while in other embodiments, the concentration is greater than 5 micromolar, greater than 10 micromolar, greater than 20 micromolar, greater than 50 micromolar, greater than 100 micromolar, greater than 200 micromolar, greater then 100 micromolar, or greater than 1 millimolar. In certain embodiments, the concentration of DFO is 100 micromolar. It should be appreciated that the concentration of DFO may be adjusted depending on the nature of the stem cells. For example, mesenchymal stem cells isolated from bone marrow may require a concentration different from hematopoietic stem cells.

The stem cells secrete stem cell factors into growth factor-free medium resulting in conditioned medium (CM). Generally, the stem cells are cultured in growth factor-free medium for approximately 72 hours before the CM is harvested. In some embodiments the CM is harvested prior to 72 hours, while in other embodiments the CM is harvested later than 72 hours, such as after 84 hours or 96 hours. In most embodiments, the stem cells are maintained at ambient conditions of 37° C. and 5% $CO_2$.

After CM is harvested, it (the harvested CM) can be filtered by ultra-filtration (using any of a variety of semi-permeable membranes) to produce processed conditioned media (pCM). In certain embodiments the pCM has an increased concentration of angiogenic factors. An increased concentration of angiogenic factors is relative to the concentration of angiogenic factors present in CM (that has not been subjected to ultra-filtration). In some embodiments, the angiogenic factors are angiogenic proteins/polypeptides. In certain embodiments, the angiogenic factors are one or more of VEGF, MCP-1, Ang-1, Ang-2, PlGF, FGF2 and PDGF-β. In some embodiments, the CM is filtered by using a filter with a 3 kD cut-off (molecule size minimum), resulting in an increase in concentration in pCM of angiogenic polypeptides that have a size greater than 3 kD.

In another aspect, the present invention is directed to compositions comprising processed conditioned medium (pCM). In certain embodiments, the composition comprises pCM and a delivery vehicle. In some embodiments, the delivery vehicle is a biocompatible or biodegradable material. In certain embodiments, the delivery vehicle is a polymer (protein matrix or mixture).

In one aspect, the composition is used to promote collateral (blood vessel branch) development in a subject. The subject may be a human or a veterinary subject. In another aspect, the composition is used to treat chronic total occlusion in a subject. In yet another aspect the composition is used to promote healing of injured tissue in a subject. For example, in certain aspects, the composition comprising pCM and a polymer is used to treat skin burns. In still other aspects, the composition is used to treat broken bones, ruptured tendons, or decubitus ulcers. The pCM may be administered in an amount effective to achieve the desired physiological effect (e.g., angiogenesis or tissue regeneration/healing).

In some embodiments, the pCM is impregnated (embedded) in the polymer. In some embodiments, the polymer is biodegradable. Rather than having to generate, for example, microspheres to deliver stem cell growth factors, the processed conditioned medium is impregnated in the polymer. As the polymer degrades, the stem cell factors are released to the injured tissue. In certain embodiments, this is particularly advantageous, for example when the impregnated polymer is used as a therapeutic bandage to treat skin burns or skin ulcerations. In some embodiments, the polymer is a gelatinous protein mixture resembling the complex extracellular environment found in many tissues. In certain embodiments, the polymer is a gelatinous protein mixture secreted by Engelbreth-Holm-Swarm (EHS) mouse sarcoma cells (e.g., Matrigel™, BD Biosciences, MD, USA). One embodiment is a therapeutic bandage, which comprises a gauze bandage impregnated with a polymer comprising CM or pCM. The resulting bandage comprises polymer/CM, polymer/pCM or polymer/CM/pCM which can be lyophilized and stored for future use. When the bandage is to be used or is applied to a wound, the lyophilized CM and/or pCM are reconstituted, either by addition of moisture (e.g., water, saline, PBS) or as a result of contact with wound moisture.

In other embodiments, the polymer is not biodegradable. For example, the non-biodegradable polymer may be used to deliver the processed conditioned medium (pCM), and after the pCM is delivered, the polymer may be discarded.

In other embodiments, the polymer permits sustained release of the processed conditioned medium. It may in a form that is injected, for example, using a needle and syringe or a needle and catheter. The polymer may be injected directly to an occluded or obstructed artery to promote angiogenesis, or directly to a site of injured tissue, for example, a ruptured tendon or broken bone to promote healing. The polymer may also be in the form of a thin, gel-like bandage. As used herein, a "therapeutic bandage" is a polymer impregnated with processed conditioned medium (pCM) that is applied topically in the form of a bandage, patch, or a configured mesh. The therapeutic bandage may be applied directly to a site of injured tissue, for example, a skin burn to promote healing of the underlying tissue. In certain embodiments, the polymer is impregnated with the pCM to form the therapeutic bandage and is used immediately to treat injured tissue. In other embodiments, the therapeutic bandage is lyophilized and stored indefinitely.

Therapeutic Uses

In one aspect, the present invention is directed to methods of promoting (enhancing or initiating) collateral development in a subject, including administering to the subject the processed conditioned medium (pCM) or any one of the compositions, described herein, in an amount effective to promote collateral development in the subject. An effective amount to promote collateral development in a subject is an amount that increases growth of new blood vessels from existing blood vessels (angiogenesis). This increase in growth of new blood vessels is relative to the amount of growth achieved in the absence of pCM or a composition comprising pCM. For example, if pCM or a composition comprising pCM is administered to the site of occlusion (obstruction) in a blood vessel, new blood vessel branches will grow at the site of administration, whereas in the absence of pCM, new blood vessels will not grow at the site of occlusion or at least not as many branches will grow. In some embodiments, the subject being treated has occlusive arterial disease, which may result in partial or total occlusion of one or more arteries. In some embodiments, the partially or totally occluded arteries supplies blood to the heart or a leg.

Collateral development is a complex process requiring multiple genes to coordinately express their products in an appropriate, time-dependent manner. Thus, in some embodiments, processed conditioned medium is administered directly to the site of arterial occlusion via multiple, sequential injections. As shown herein, using the conditioned medium or processed conditioned medium secreted by stem cells allows for the delivery of multiple factors supporting collateral development, including both angiogenic and arteriogenic factors, to any site requiring collateral development. Delivery may be by surgical or percutaneous (e.g., catheter-based) means.

In another aspect, the present invention is directed to methods of treating chronic total occlusion (CTO) in a subject, including administering to the subject processed conditioned medium or any one of the compositions, described herein, in an amount effective to treat the CTO in the subject. A CTO refers to an artery that has been occluded for an extended amount of time (e.g., approximately 30 days). An amount effective to treat chronic total occlusions is one that increases growth of new blood vessels from existing blood vessels (angiogenesis), permitting blood flow to bypass the CTO through the new blood vessel branches to reach, for example, the heart or leg. In some embodiments, the subject may be at risk of having a myocardial infarction (e.g., blockage of blood vessels to the heart inhibiting (totally or partially) passage of oxygen to the heart).

In yet another aspect, the present invention is direct to methods of treating injured tissue in a subject, including administering to the subject any one of the compositions, described herein, in an amount effective to treat the injured tissue in the subject. The injured tissue may be burned tissue/skin, tissue/skin damaged from grafting (e.g., when undamaged skin is taken from one part of the body to function as donor skin for another part of the body), a ruptured tendon or broken bone, a decubitis ulcer or other skin ulceration. An amount effective to treat an injured tissue is an amount that decrease (reduces) the amount of time for healing of the tissue. This decrease in time is relative to the time it would take for the injured tissue to heal in the absence of processed conditioned medium. For example, In still another aspect, the present invention is direct to methods of treating a skin burn in a subject, including administering to the subject any one of the compositions, described herein, in an amount effective to treat the skin burn in the subject. An amount effective to treat the skin burn is one that decreases the amount of time for healing of the burned skin or regeneration of the underlying skin. In some embodiments, the method comprises removing a layer of burned dead skin to expose the underlying skin layer, grafting healthy skin over the underlying layering, and administering pCM or a composition comprising pCM to the grafted skin layer. In certain embodiments, a therapeutic bandage, as described herein, is administered to the burn site.

It is to be understood that in any of the foregoing aspects and embodiments, conditioned medium comprising factors secreted by stem cells may be used in place of or in addition to processed (filtered or ultra-filtered) conditioned medium.

"Treatment," "treat," or "treating," as used herein covers any treatment of a human or nonhuman (e.g., cat, dog, horse, etc.), and includes preventing the disease or condition from occurring in a subject who may be predisposed to the disease or condition but has not yet been diagnosed as having it, for example, a subject at risk of developing a myocardial infarction. It also includes inhibiting (arresting development of), relieving or ameliorating (causing regression of), or curing (permanently stopping development or progression) the disease or condition.

As used herein, the terms "a" or "an" means one or more; at least one.

The present invention is further illustrated by the following Examples, which in no way should be construed as further limiting. The entire contents of all of the references (including literature references, issued patents, published patent applications, and co-pending patent applications) cited throughout this application are hereby expressly incorporated by reference.

EXAMPLES

Stem cells derived from the bone marrow are factories that secrete many growth factors and other molecules than have major effects on multiple pathways (FIG. 1) [T. Kinnaird, E. Stabile, M. S. Burnett, C. W. Lee, S. Barr, S. Fuchs, S. E. Epstein. Marrow-Derived Stromal Cells Express Genes Encoding a Broad Spectrum of Arteriogenic Cytokines and Promote In Vitro and In Vivo Arteriogenesis Through Paracrine Mechanisms *Circ Res.* 2004; 94:678 685]. This finding led to an entirely novel therapeutic strategy that involves using what stem cells secrete, rather than using stem cells directly. When embedded into a biodegradable polymer (the "therapeutic polymer"), the resulting sustained release of the stem cell-derived molecules improve collateral function. "Therapeutic bandages," containing the stem cell-derived molecules embedded in a biodegradable bandage-like material may also be used to treat injured tissue, with implications for treating burns, ruptured tendons broken bone, and decubitis ulcers.

Example 1

Conditioned Medium Retrieval and Processing

Figure 2:
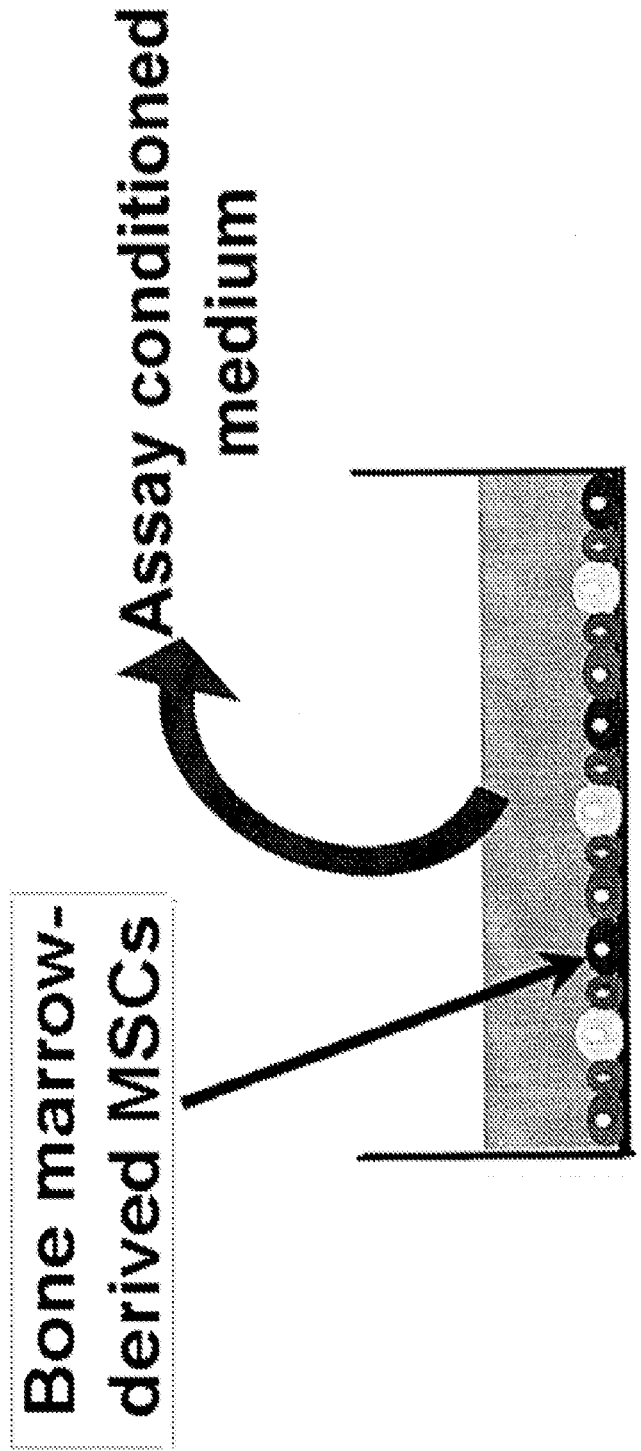
FIG. 2 depicts conditioned medium (CM) covering bone marrow-derived mesenchymal stem cells (MSCs).

Media of low passage multipotent stem cells (at the highest possible confluence level) was changed to a growth factor-free, serum-free, phenol red-free DMEM+100 µM Desferroxamine (DFO, Sigma Aldrich, Cat #D9533). After 72 hours of incubation in a normal cell culture environment (Temp=37° C., $CO_2$=5%), medium covering the cells was collected. FIG. 2 depicts conditioned medium (CM) covering, for example, stem cells isolated from bone marrow.

After collection (harvest) of the CM, cellular debris was removed with centrifugation. The conditioned medium was subsequently subjected to serial rounds of ultra-filtration using filter size 3 kD (Amicon Ultra Centrifugal Filter Units, Millipore, Cat#UFC900324), resulting in the purification, desalting, and concentration of the molecules larger than the filter pore size (including the angiogenic proteins) and the generation of processed CM.

The processed CM was assayed for the presence of the angiogenic agents: vascular endothelial growth factor (VEGF), fibroblast growth factor-2 (FGF2), and angiopoetin-1 (ANG-1).

Example 2

Angiogenic Potential of Processed Conditioned Medium

Figure 3:
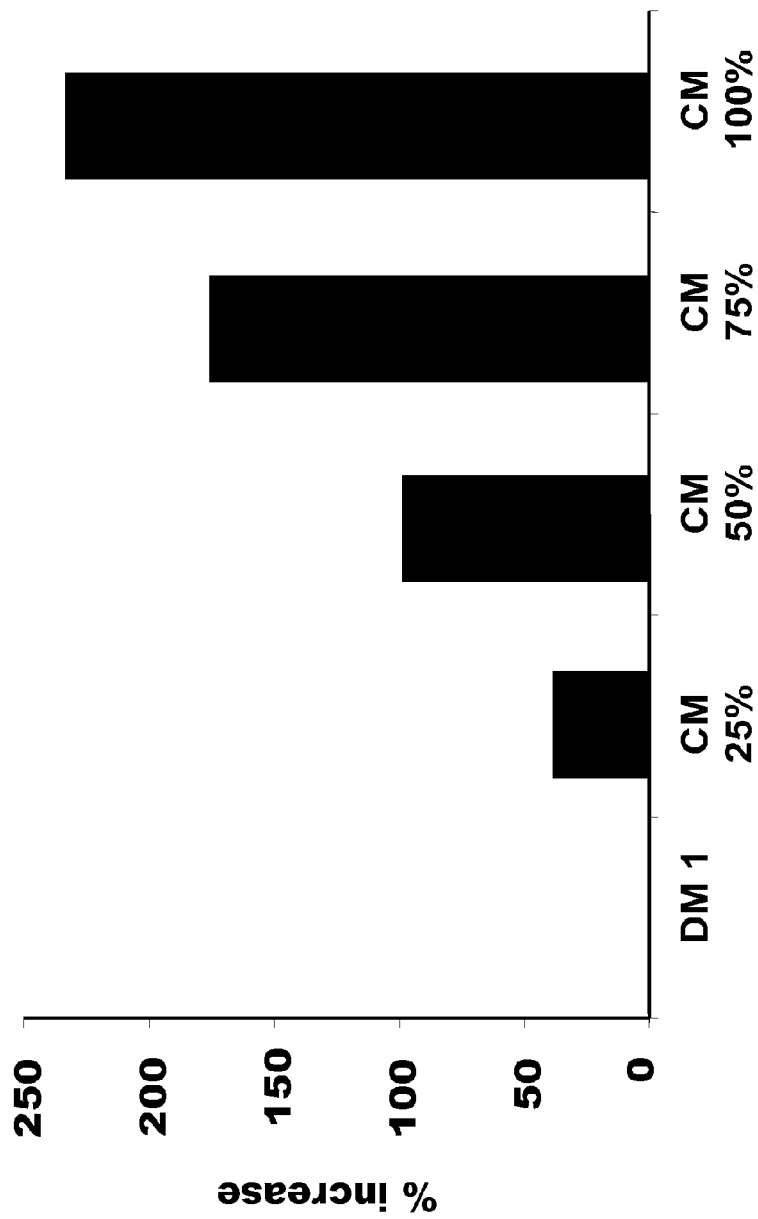
FIG. 3 is a graphic representation of data demonstrating that there is a dose response in endothelial cell proliferation to concentration of CM in vitro. DMI=FBS 1%.

The angiogenic potential of secreted factors in processed conditioned (CM) produced using bone marrow stem cells was evaluated. A key component of angiogenesis, endothelial cell proliferation, was measured. FIG. 3 shows a dose response in endothelial cell proliferation to concentration of CM in vitro. Endothelial cell proliferation increases with increased dosages of processed CM, demonstrating that the processed CM has angiogenic potential.

Example 3

Stem Cells Secrete Angiogenic Agents

Figure 4:
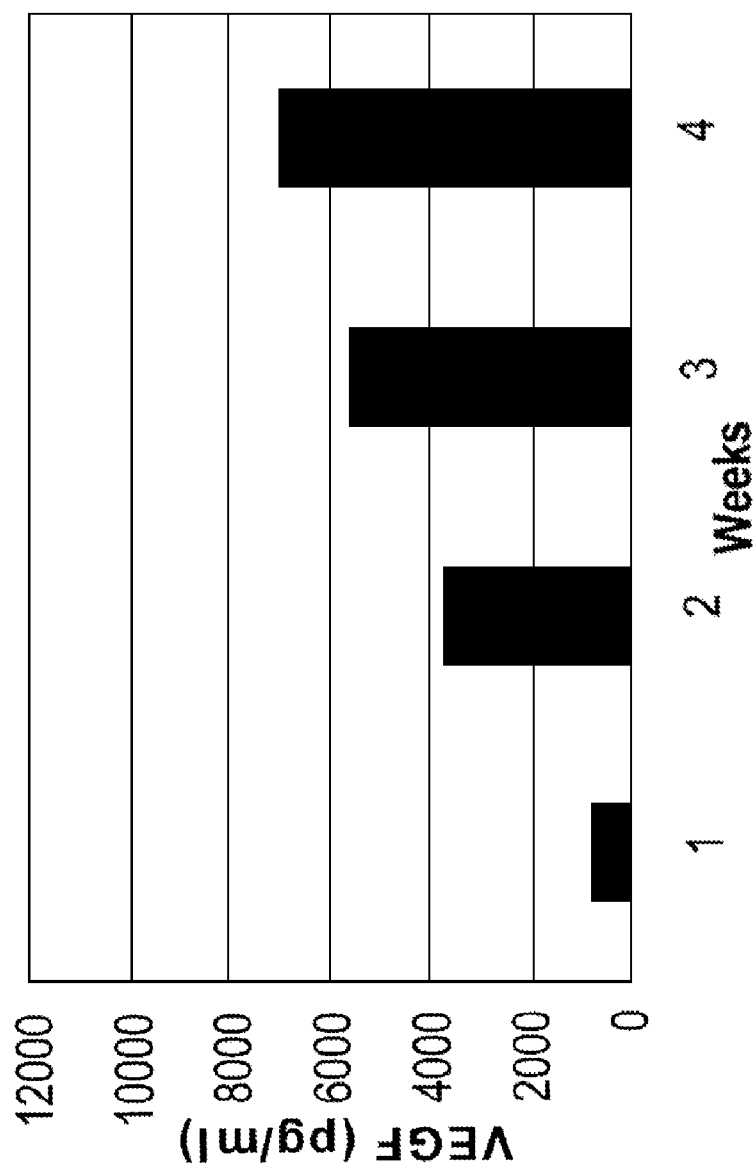
FIG. 4 is a graphic representation of data demonstrating that human bone marrow-derived MSCs produce an angiogenesis factor, vascular endothelial growth factor (VEGF).
Figure 5:
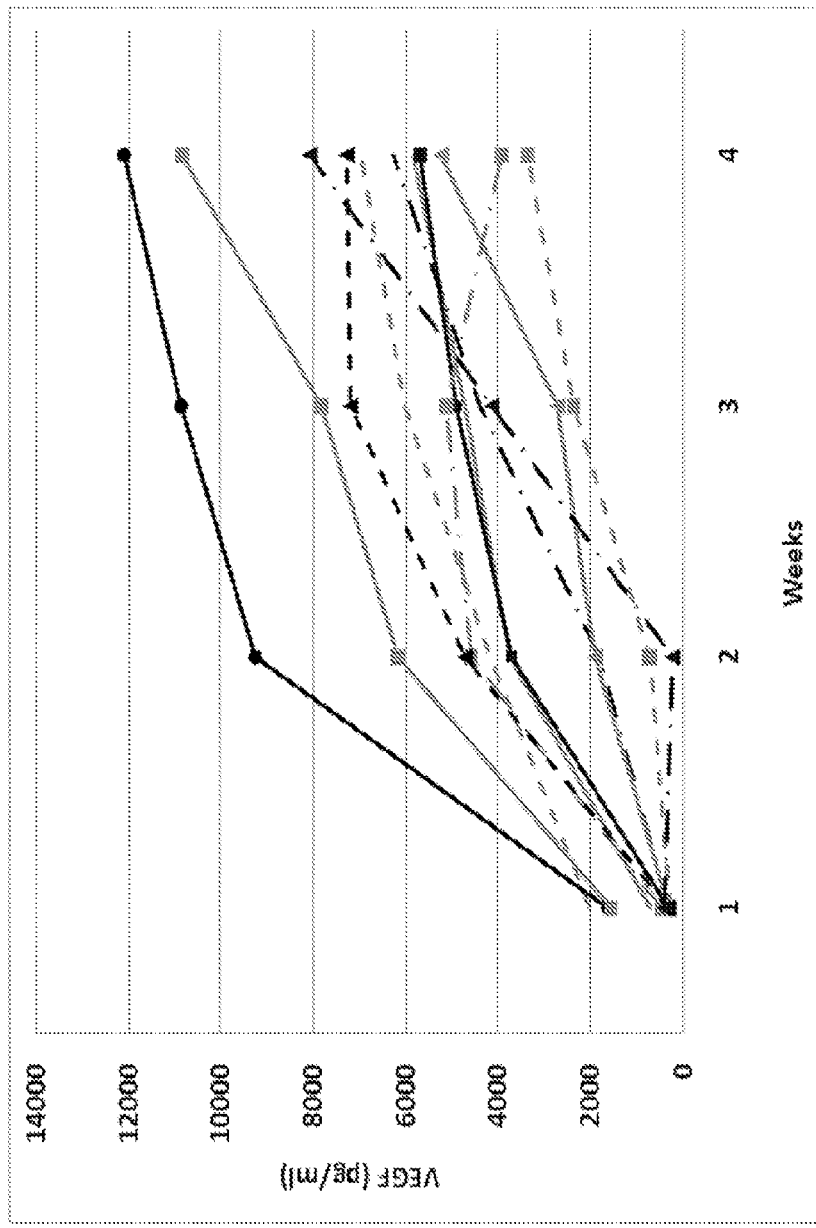
FIG. 5 is a graphic representation of data demonstrating that the concentration of VEGF secreted by bone marrow-derived MSCs varies among patients.

FIGS. 4 and 5 demonstrate that cultured human bone marrow stem cells secrete angiogenic factors, including vascular endothelial growth factor (VEGF), and that the concentration of such factors varies among patients. It should be noted that some patients secrete very low concentrations of VEGF. These patients may be particularly good candidates for CM therapy.

Example 4

Optimal Growth Conditions for the Secretion of Angiogenic Agent

Figure 6:
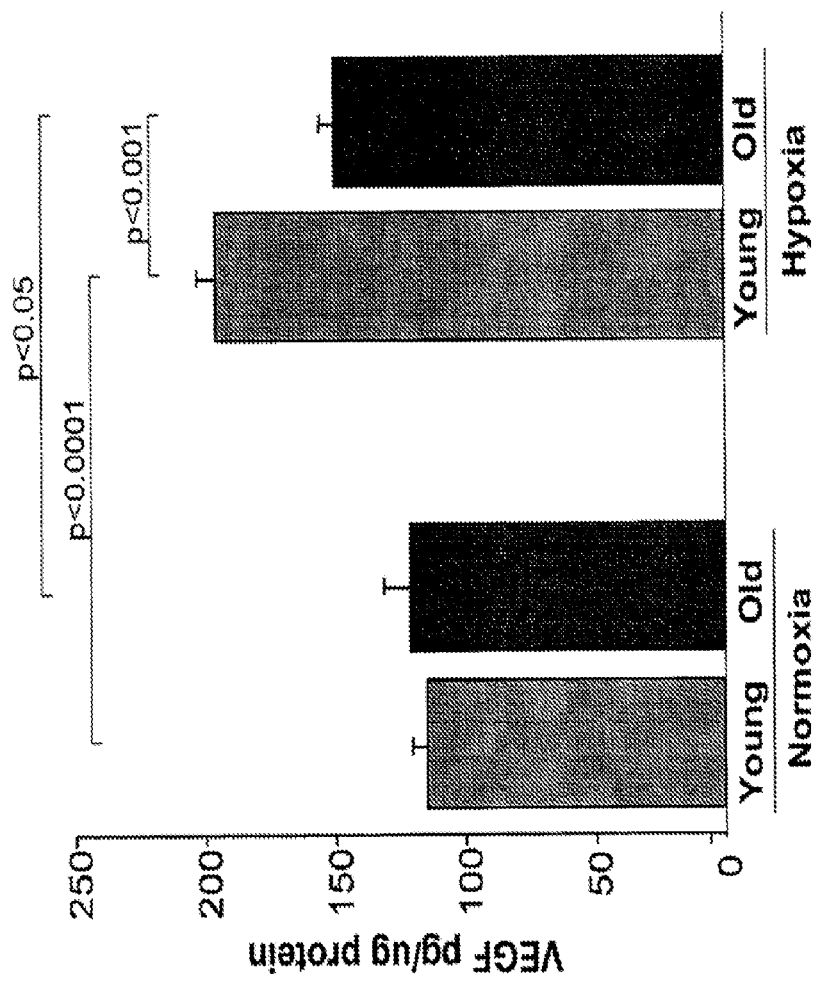
FIG. 6 is a graphic representation of data demonstrating the effects of hypoxia on MSCs derived from young and old mice. Under hypoxic conditions, there is a statistically significant increase in the concentration of VEGF secreted by young mice compared to old mice. There is also a statistically significant increase in the concentration of VEGF secreted by young mice under hypoxic conditions as compared to young mice under normal conditions (normoxia).

Angiogenesis is induced by hypoxia, and when grown under hypoxic conditions stem cells, for example, mesenchymal stem cells (MSCs) produce increased concentrations of VEGF protein (FIG. 6). It should be noted that stem cells obtained from old mice are not as robust as cells obtained from young mice in responding to hypoxia by increasing VEGF. This provides evidence indicating that older patients, whose own stem cells are poor secretors of angiogenic cytokines, may be particularly good candidates for CM therapy—in particular, CM obtained from stem cells derived from young healthy individuals (allogeneic stem cells).

Figure 7:
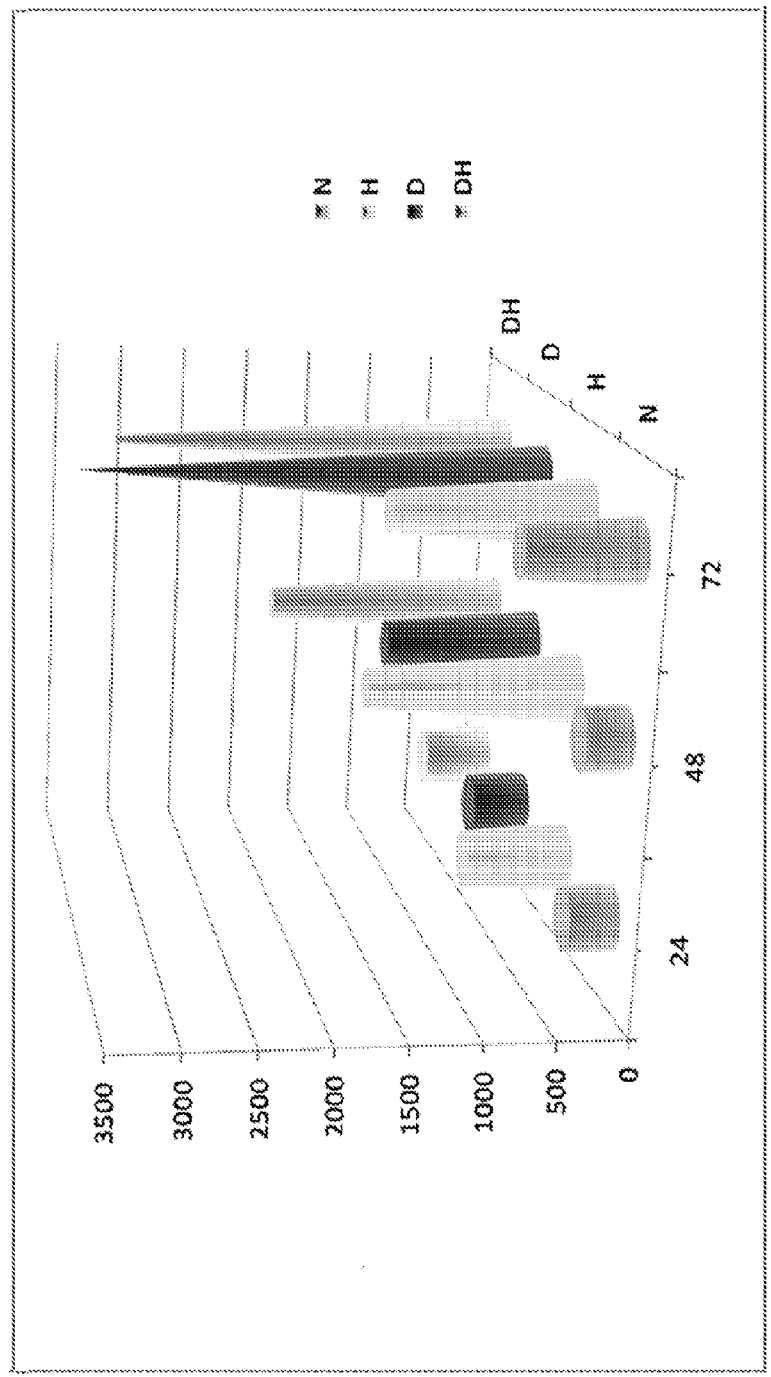
FIG. 7 is a graphic representation of data showing secreted VEGF levels from MSCs grown under conditions of normoxia, hypoxia, stimulation with deferroxamine (DFO), or hypoxia plus DFO for 24, 38, or 72 hours.

A major hypoxia-induced pathway is the hypoxia-inducible factor-1 (HIF-1) pathway. HIF-1 is a heterodimeric transcription factor that regulates expression of genes involved in oxygen homeostatis, including VEGF. The HIF-1 pathway is stimulated by desferroxamine, a chelator of iron, which inhibits the HIF-1 pathway. Therefore, the levels of prototypic angiogenesis factors, VEGF, PDGF, FGF, and Ang-1 were assayed by ELISA when mesenchymal stem cells (MSCs) were grown under conditions of normoxia, hypoxia, DFO, or hypoxia plus DFO for 24, 48, or 72 hours (FIG. 7 shows VEGF levels). Data collected from this assay demonstrated that optimal secretion of VEGF into the conditioned media occurred when MSCs were treated with DFO for 72 hours. This constitutes the growth conditions that were used for the following polymer matrix studies. These results imply that any intervention that stimulates the HIF could be used to stimulate stem cells to secrete angiogenic factors, including DFO.

Figure 8:
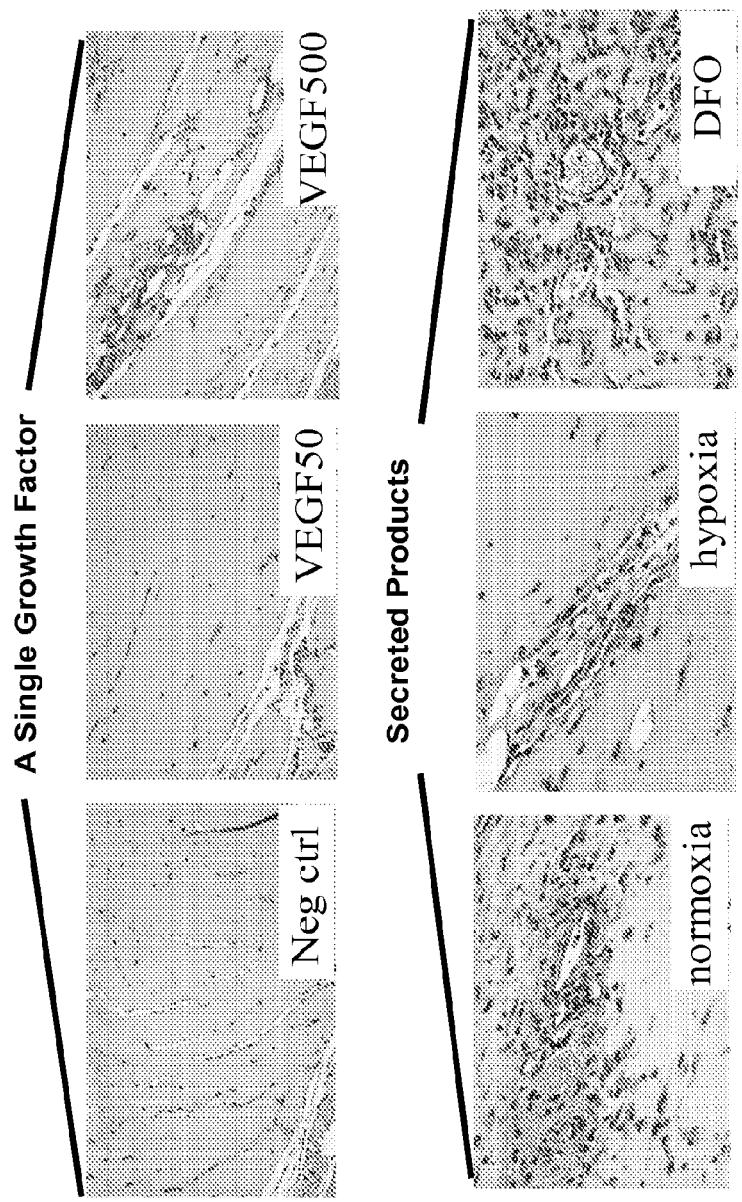
FIG. 8 shows histological sections from mice abdomens post implantation with CM-impregnated polymer, VEGF-impregnated polymer, or a control. The data demonstrates that the secreted stem cell factors are more efficient at stimulating growth of blood vessels, as compared to VEGF alone. The data also demonstrates that CM collected from cells grown in DFO are more efficient at stimulating growth of blood vessels, as compared to cells grown in the absence of DFO.

To demonstrate the effects of the conditioned media on angiogenesis in vivo, a polymer (Matrigel™) was impregnated with VEGF (at two concentrations) (FIG. 8, upper panel). Polymer without growth factor was used as a control. Stem cells were grown under different conditions (normoxia=normal oxygen levels, hypoxia=low oxygen levels, or stimulated by DFO (FIG. 8, lower panel). Under each of the conditions, the secreted products of stem cells were more potent in growing blood vessels than VEGF. Blood vessel development was evidenced by presence of the purple staining cells, and the circular structures (lower right panel) that, because they contain red blood cells, are identified as blood vessels.

Example 5

In Vivo Biological Effects of Polymer Matrix on Angiogenesis—Plug Assays

Culture-expanded human MSCs were washed to remove traces of serum growth factors and bathed in serum-free medium containing 100 µM DFO for 72 hours. Conditioned medium (CM) was then aspirated and its cellular debris were eliminated with centrifugation. Serial rounds of ultra-filtration using filter size of 3 kD (Millipore) was then utilized to achieve purification, desalting, and concentration of CM. Concentrated CM (CCM) was characterized by ELISA (R&D) for the presence of VEGF.

In vivo angiogenesis was measured by polymer matrix plug assay. Male C57 Bl/6 mice (Jackson) were subcutaneously injected with Matrigel™ containing CCM (CCM50), 10-fold diluted CCM (CCM5), recombinant human VEGF (rh-VEGF) at a similar concentration of VEGF measured in CCM (50 ng/ml, VEGF50), or phosphate buffered saline (PBS) as the negative control (n=6 per group).

Figure 10A:
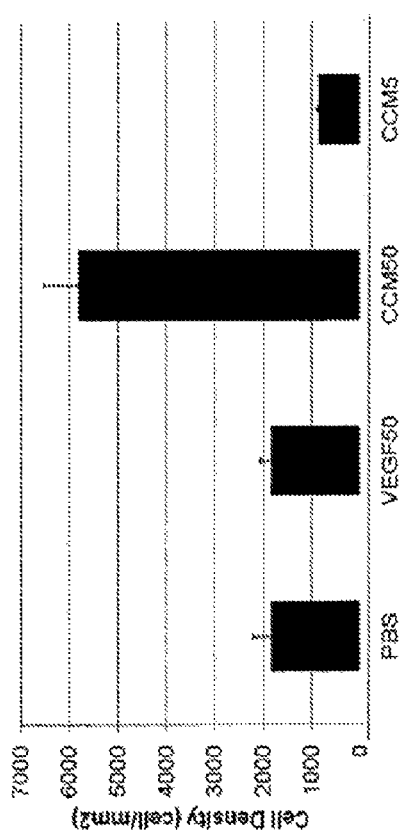
FIGS. 10A-10D are graphic representations of endpoint data collected from the experiment described in FIG. 9: (A) Cell density (cells/mm2) (FIG. 10A), (B) Number of RBC-containing vessels/200× field (FIG. 10B), (C) Sum area of RBC-containing vessels/200× field (FIG. 10C), and (D) Number of CD31+ vessels/100× field (FIG. 10D).
Figure 10B:
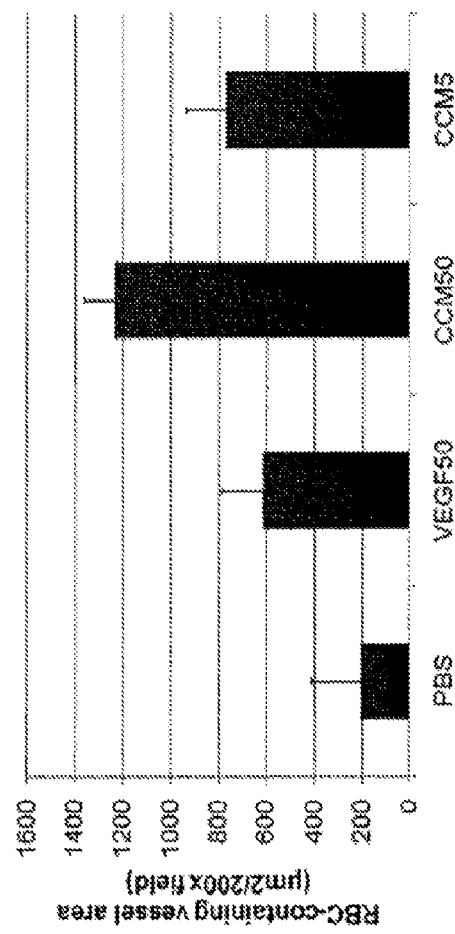
Figure 10C:
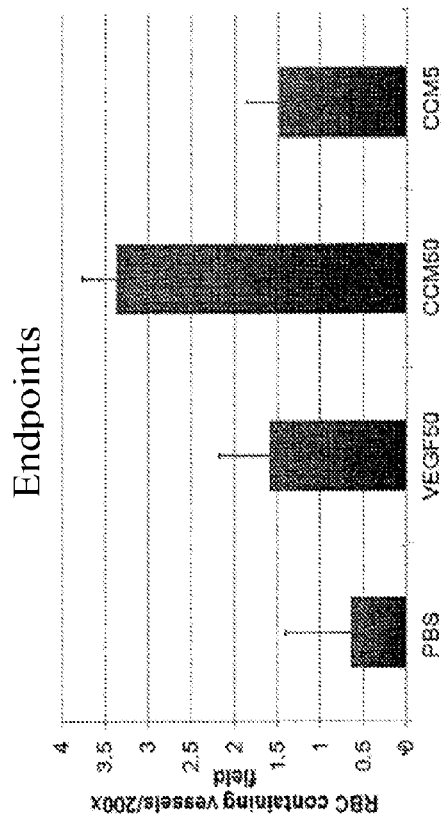
Figure 10D:
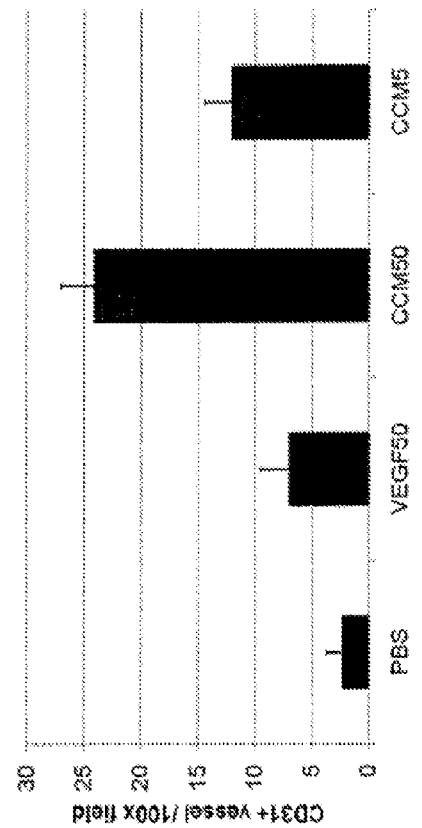

After 14 days, plugs were harvested and stained with Hematoxylin and Eosin (H&E) and anti-CD31 (FIG. 9). Endpoints included: (a) Cell density (cells/mm2) (FIG. 10A), (b) Number of RBC-containing vessels/200× field (FIG. 10B), (c) Sum area of RBC-containing vessels/200× field (FIG. 10C), and (d) Number of CD31+ vessels/100× field (FIG. 10D). Five slides were quantified for each animal. All measurements were performed by blind observers using Image Pro Plus software for image analysis.

Compared to a similar concentration of rh-VEGF when used alone, CCM resulted in greater density of cells (5817 vs 1844 cell/mm2, P=0.003), red blood cell-containing vessels (3.37 vs. 1.60 vessel/high power field (PF), P=0.04), and CD31+ vessels (24.1 vs. 7.0 vessel/low PF, P<0.001). A dose response relationship was observed: CCM at 1/10th concentration resulted in lower density of cells (867 cell/mm2, P<0.001), red blood cell-containing vessels (1.49 vessel/high PF, P=0.002), and CD31+ vessels (12.1 vessel/low PF, P=0.02).

Growth/paracrine factors released by human MSCs have superior angiogenic capacity in a Matrigel™ plug assay than rh-VEGF alone (when VEGF is administered at identical concentrations as in CCM). This suggests that the multiple pro-angiogenic factors secreted by MSCs exert synergistic angiogenic effects when compared to that provided by a single potent angiogenic factor. It follows that cell-free CM of MSCs may provide a promising therapeutic strategy for enhancing collateral function in ischemic vascular disease (FIG. 11).

Example 6

Treatment of Chronic Total Occlusion

Chronic total occlusion (CTO) of a coronary or peripheral artery is often caused by a ruptured plaque producing a thrombus (FIG. 12A, upper schematic). Over time the thrombus organizes and is replaced by scar tissue (FIG. 12A, lower schematic). With CTO, during manipulation of the guide wire through the CTO (FIG. 12D), there is a small risk that the wire will perforate the vessel wall, a serious complication. Many patients with CTO are not good surgical candidates, thus, catheterization-based procedures (PCI) remain the only option. However, the failure rate of PCI treatment for CTO is high, and even when PCI is successful, the duration of the procedure is usually long, requiring significant radiation to the operator and to the patient. It also requires high volumes of dye to be injected for visualization of lesion and catheter, which increases the risk of the patient developing renal problems.

To circumvent these obstacles, a catheter has been designed that allows for local injection of the biodegradable polymer into a vessel wall just at the site of chronic total occlusion. FIG. 13 shows a micro-infusion catheter designed by Mercator MedSystems, Inc. The catheter is designed to allow injection of the therapeutic agent being tested directly into the arterial wall. As the catheter is advanced to the chronic total occlusion, the needle contained within the catheter is prevented from injuring the vessel wall during advancement by being enfolded in a thick-walled balloon. Once the catheter is positioned appropriately, the balloon is inflated and eccentrically expands, extruding the needle into the vessel wall. The needle protrudes minimally, so that the injection is placed within the arterial wall, and not the surrounding tissue.

This catheter is currently being used in clinical trials without complications. A specially designed catheter is being fabricated for use in future rabbit studies of CTO. By embedding the stem cell products within a polymer, and using the specially designed catheter to deliver the "therapeutic polymer" to the site of total occlusion, the goal is to convert a totally obstructed artery into one that has robust collaterals capable of delivering the requisite amounts of blood to the heart.

Example 7

Treatment of Injured Tissue

Figure 14B:
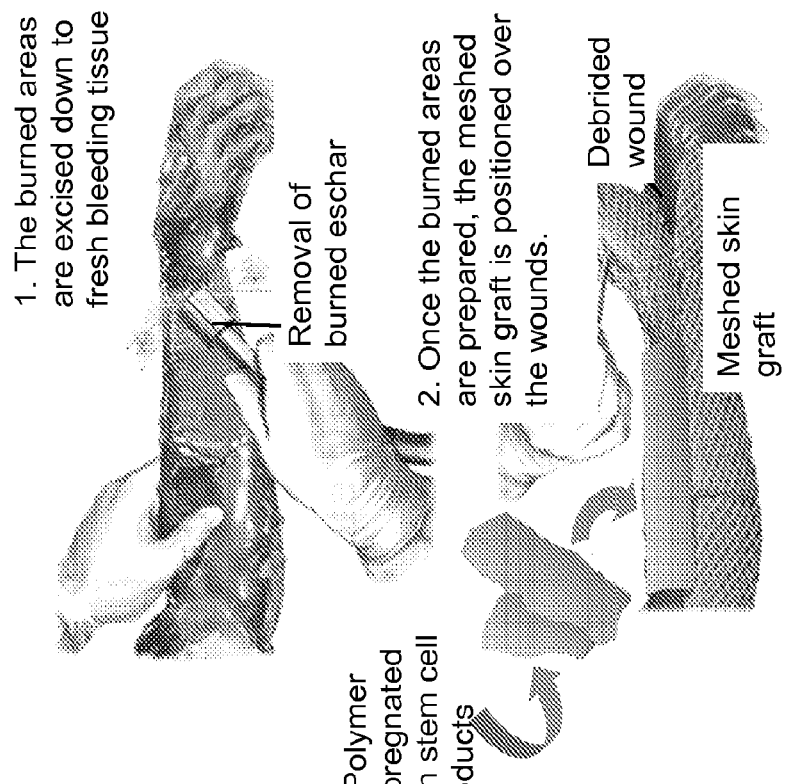
FIGS. 14A and 14B is a schematic of treatment of skin burns using a CM-impregnated therapeutic bandage (CM-impregnated polymer matrix).
Figure 14A:
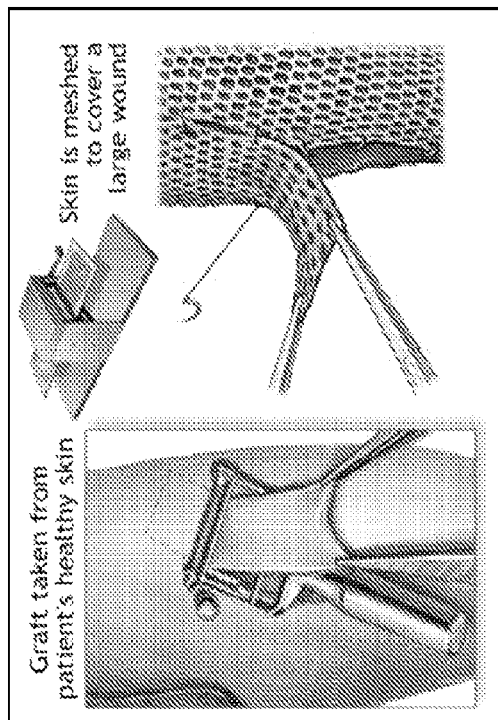
Figure 15:
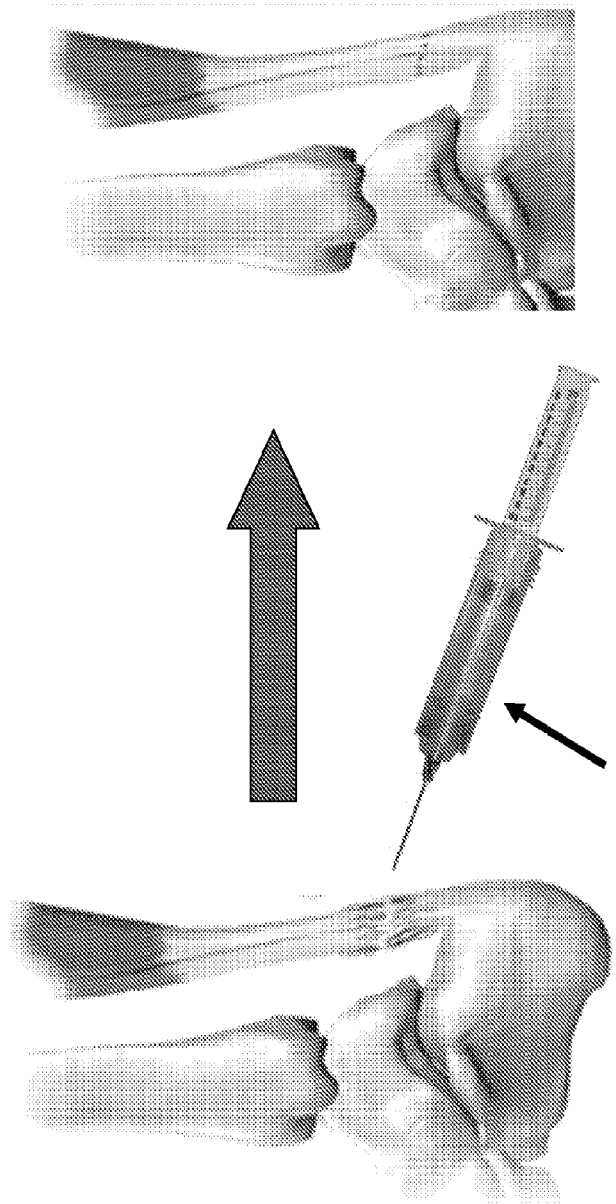
FIG. 15 is a schematic of treatment of ruptured tendon by injecting CM-impregnated polymer directly to the site of injury.

The CM-embedded polymer matrix may be used to facilitate healing of injured tissue, including broken bone, torn tendons, decubitis ulcers, and burned skin. For example, healthy skin is taken from unaffected areas (FIG. 14A, left panel), and used to cover the burned skin. If the area of the skin defect is especially large, the harvested skin may be meshed to stretch it into a larger patch (FIG. 14A, right panel). This leaves spaces between the cell-rich skin and the spaces created by the meshing, causing a longer time-line for complete healing to take place. The burned dead skin (eschar) is removed, the meshed skin graft is applied to the burned area, and then the CM-embedded polymer matrix, or "therapeutic bandage," is applied (FIG. 14B). This biodegradable polymer matrix will gradually degrade, slowly releasing the stem cell products, which will facilitate the development of blood vessels. The stem cell products and newly formed vessels will facilitate "take" of skin graft and also promote the proliferation of normal skin cells—all resulting in a facilitation of healing.

Example 8

Treatment of Ruptured Tendon

The CM-embedded polymer matrix is administered to a ruptured Achilles tendon at the time of injury (or shortly thereafter) to facilitate healing of the tendon.

Example 9

Efficacy of Conditioned Media Derived From Multistem Cells for Enhancing Collateral Function The in vivo efficacy of conditioned media of MultiStem Cells for enhancing collateral function is demonstrated as described in this example, in which collateralogenesis is assessed in three groups: concentrated or processed conditioned medium, PBS-embedded (negative control) and VEGF-embedded (positive control). In the three groups, a biodegradable polymer is embedded with pCM, PBS (negative control) or VEGF (positive control), respectively. Results show whether CCM embedded in a biodegradable polymer and implanted in the adductor region results in greater collateralogenesis than a PBS-embedded polymer.

Endpoints—
1. Primary
   a. Hindlimb blood flow recovery: ratio of blood flow in the ischemic leg to non-ischemic leg, measured by laser Doppler immediately after ligation, and thereafter on days 3, 7, 14, 21, and 28 (6 measurements for each animal)

2. Secondary
   a. Blood vessel density: ratio of the blood vessel density in the ischemic to nonischemic leg. H&E, CD31, and alpha-SMA immunohistochemistry are used to identify blood vessels (measured in the thigh, in the region of known collateral development).

Summary of Intervention—

Depending on the study group, CCM, rh-VEGF, or PBS is embedded in biodegradable polymer (Hydrogel). Young Balb-C male mice will undergo femoral artery ligation. Hydrogel containing the therapeutic material is implanted in the adductor region. Blood flow will be measured at certain time points over the course of 28 days. Animals are euthanized after the last blood flow measurement and their tissues (including adductor muscles) collected for histology. Histologic assessments include H&E staining, immunohistochemistry for alpha smooth muscle actin, and immunohistochemistry for CD31.

Rationale—

The process of collaterogenesis takes place over 7-10 days. Therefore, it is desirable to increase the duration of protein activity at the location of growing blood vessels. A very appealing way to overcome this problem is to take advantage of emerging polymer technology. Polymer particles can be manufactured in a way that they release their content in a fairly precise time-specific manner. It would therefore be possible to use these particles in vivo to release proteins over an extended period of time, which is necessary to achieve a biological significant collaterogenic effect.

CM Processing—

Media of low passage multistem cells (at the highest possible confluence level) are changed to a growth-factor-free, serum-free, phenol-red-free DMEM+100 µM DFO (Sigma Aldrich, Cat #D9533). After 72 hours incubation at normal cell culture environment (Temp=37° C., $CO_2$=5%), medium covering cells are collected and processed further. Cellular debris is removed with centrifugation and the resulting CM is subjected to serial rounds of ultrafiltration using filter size 3 kD. The result is purification, desalting, and concentration of the molecules larger than the filter pore size (including the angiogenic proteins). The pCM or CCM (concentrated CM) is ready to be embedded in hydrogel and then administered to mice.

Hindlimb Ischemia Model—

The hindlimb ischemia model is one of the most extensively used animal models for the study of adult collateral function and strategies aimed to improve function in vivo. In this model, collaterogenesis of the ischemic hindlimb occurs spontaneously mainly through remodeling of existing collaterals—this process is usually called arteriogenesis. Such revascularization can be measured functionally using blood flow recovery as measured by Laser Doppler. Thus, immediately following ligation of the femoral artery, the blood flow to the distal leg is significantly diminished, leading to ratio of blood flow in the operated leg to the blood flow in the non-ligated leg of around 0.1 (normal ratio is around 1.0 as both legs have similar blood flow prior to ligation). Over the course of a few weeks, blood flow in the operated leg gradually increases, rarely to normal pre-ligation values. This model is used to assess the therapeutic role of CM on arteriogenesis.

Study Design—

Processed CM is incorporated into a biodegradable polymer (Hydrogel) and injected in the adductor region of the animal's hindlimb.

This biodegradable polymer provides a "timed-release" delivery system for delivering the CM at appropriate concentrations over 7-10 days, which is important for efficient arteriogenesis. The importance of such delivery systems have been shown for single growth factors in the past (Mooney et al., FASEB J. 2007 December; 21(14):3896-903)

Animals are followed for 28 days and blood flow in the operated limb is measured immediately after the surgery and on days 3, 7, 14, 21 and 28 after surgery. The ratio of blood flow in operated to non-operated limb serves as a primary endpoint. There are a total of 3 groups, all with test substance implanted in the adductor region (which contains developing collaterals):

1) pCM processed conditioned medium is embedded in the hydrogel plug,
2) Negative control: PBS (Phosphate Buffer Solution) which does not contain any active arteriogenic constituent is embedded in the hydrogel plug,
3) Positive control: recombinant human VEGF at a previously established concentration (FASEB J. 2007 December; 21(14):3896-903) is embedded in the hydrogel plug, The primary endpoint is compared among the 4 groups using RM (repeated measures) ANOVA test.

Animals—

The strain used is a model for hindlimb ischemia to demonstrate efficacy of an intervention believed to enhance collateral flow is the Balb-C. This strain has a poor collateral flow recovery response and therefore provides the most room to demonstrate improvement, if such does in fact occur.

Statistics—

Repeated measures of ANOVA (RM-ANOVA) are used to compare the 4 groups. Boneferonni test will be used to control for multiple testing. All analyses is performed using either Stata or SAS softwares. Statistical significance is accepted if the value (two tailed) is less than 0.05.

Sample Size—

20 per group (total of 60 in 3 groups).

The invention claimed is:

1. A method of producing processed conditioned medium, comprising:
   (a) culturing stem cells in growth-factor-free medium comprising desferroxamine, wherein the stem cells have been previously cultured in growth medium, thereby generating conditioned medium that comprises factors secreted by the stem cells;
   (b) harvesting the conditioned medium; and
   (c) filtering the conditioned medium to produce processed conditioned medium.

2. The method of claim 1, wherein the filtering is by ultrafiltration.

3. The method of claim 1, wherein the processed conditioned medium comprises an increased concentration of angiogenic factors.

4. The method of claim 1, wherein the stem cells are isolated from bone marrow or adipose tissue.

5. The method of claim 4, wherein the stem cells are isolated from bone marrow and are mesenchymal stem cells.

6. The method of claim 4, wherein the stem cells are isolated from bone marrow and are hematopoietic stem cells.

7. A method of enhancing secretion of angiogenic factors by stem cells, comprising culturing the stem cells in growth factor-free medium comprising desferroxamine.

8. The method of claim 7, wherein the stem cells are isolated from bone marrow or adipose tissue.

9. The method of claim 8, wherein the stem cells are isolated from bone marrow and are mesenchymal stem cells.

10. The method of claim 8, wherein the stem cells are isolated from bone marrow and are hematopoietic stem cells.

* * * * *